United States Patent [19]

Levy

[11] Patent Number: 5,611,433
[45] Date of Patent: Mar. 18, 1997

[54] MEDICAL SPECIMEN SLIDE MAILER WITH IMPROVED SPECIMEN PROTECTION

[76] Inventor: Abner Levy, 325 N. Oakhurst Dr., P4, Beverly Hills, Calif. 90210

[21] Appl. No.: 654,550

[22] Filed: May 29, 1996

[51] Int. Cl.[6] .................................................. B65D 75/14
[52] U.S. Cl. ........................ 206/569; 206/775; 206/784
[58] Field of Search .................................. 206/569, 570, 206/775, 782, 486, 784

[56] References Cited

U.S. PATENT DOCUMENTS 4,078,656  3/1978  Crane et al. ..................... 206/570 X
4,979,515  12/1990  Briggs et al. ..................... 206/569 X Primary Examiner—Jacob K. Ackun
Attorney, Agent, or Firm—Beehler & Pavitt

[57] ABSTRACT

A mailer for medical specimen slides is made of a sheet of relatively stiff material cut, scored and folded to make a base and a cover each having a double thickness of the sheet material and joined along a hinge line. One thickness in the base is cut to define a slide holding well for holding a specimen slide, and one thickness in the cover is cut to define a clearance recess overlying the holding well in a closed condition of the mailer to avoid contact between the cover and a specimen bearing portion of the specimen slide. Preferably the cover is also cut to define a window opening positioned for exposing to view an end portion of the holding well corresponding to a frosted end portion of the specimen slide in the well.

13 Claims, 2 Drawing Sheets

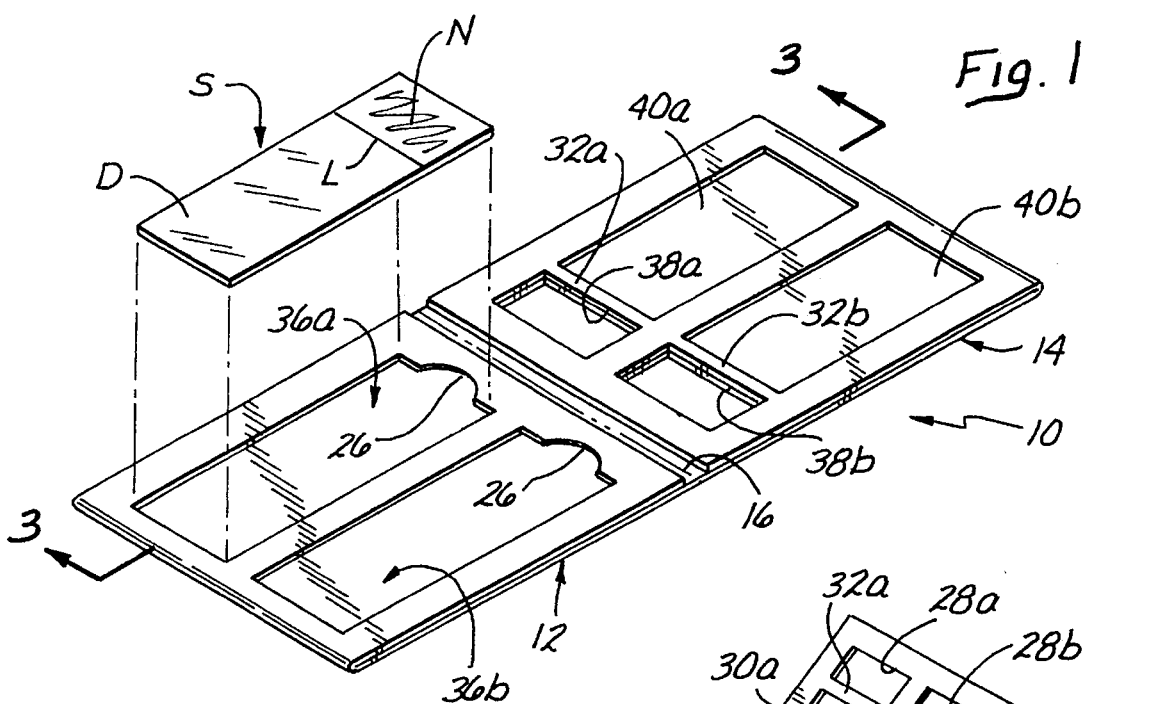
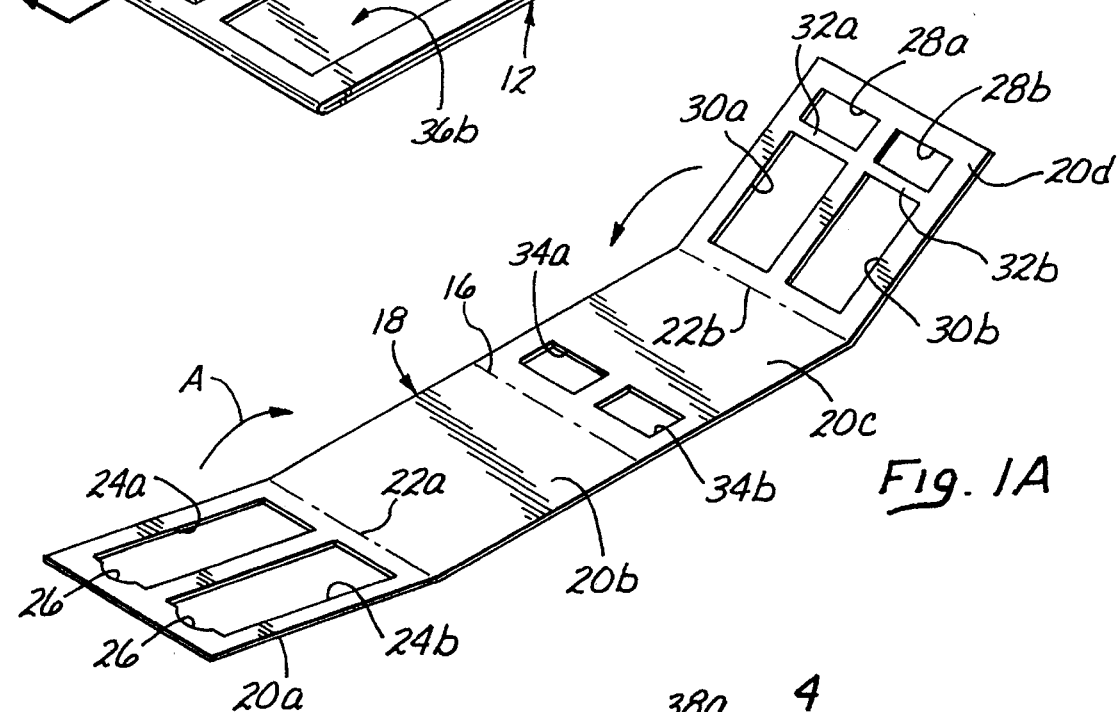
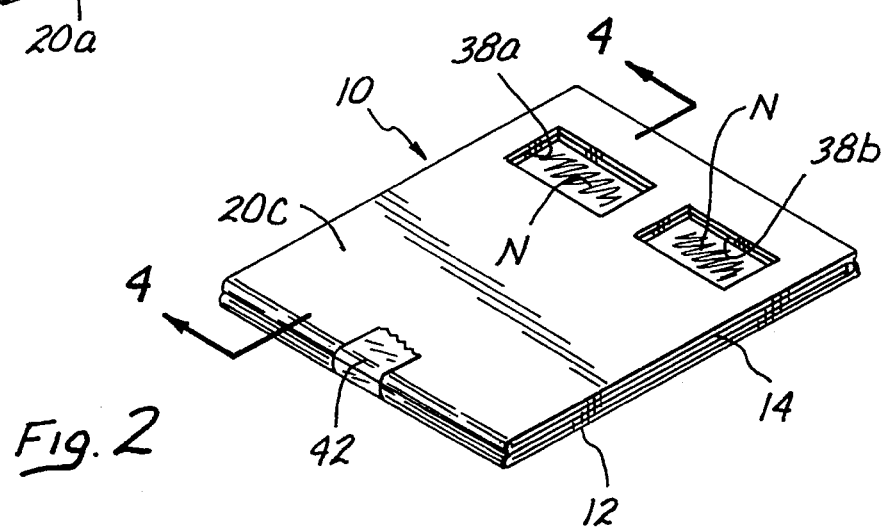

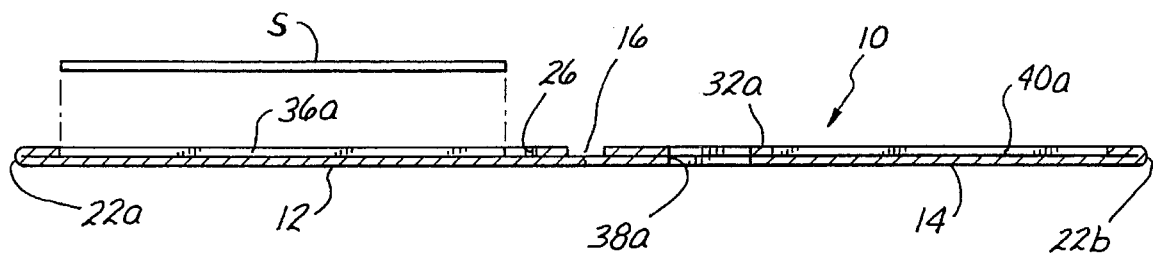
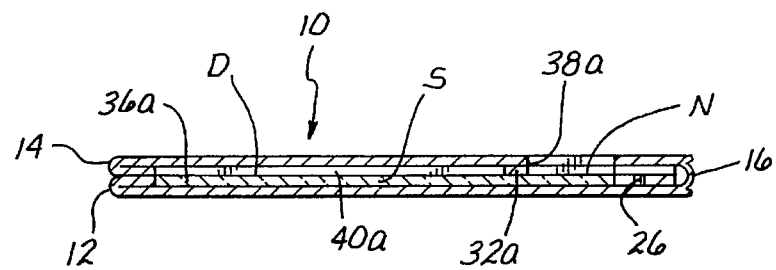
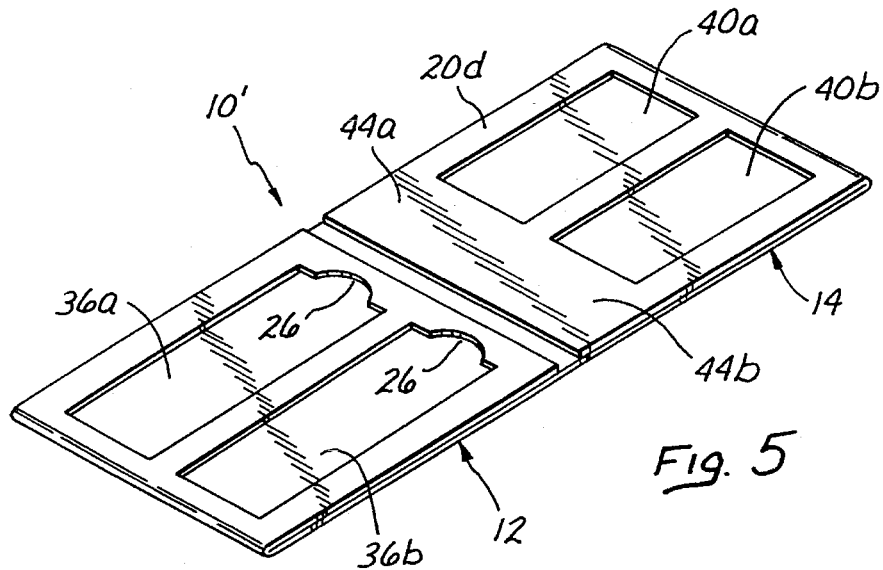

MEDICAL SPECIMEN SLIDE MAILER WITH IMPROVED SPECIMEN PROTECTION

BACKGROUND OF THE INVENTION

1. Field of the Invention

The present invention pertains to protective holders, carriers and mailers used for packaging medical specimen slides during transport from a specimen collection site to a clinical laboratory for analysis.

2. Background of the Invention

It is common clinical practice during medical examinations to take biological specimens from a patient consisting of tissue or fluid samples. The specimens are usually sent to a clinical laboratory for study, in order to diagnose disease in its earliest possible stages where the chances of a cure are greatest. Small amounts of tissue or fluids are collected from the patient's body and deposited on the surface of a specimen slide, which is usually an elongated rectangle of thin glass. One end portion of the slide, approximately one quarter of the slide surface, is frosted to provide a writing surface on which patient or other specimen identifying information can be written with a suitable marker.

A most common type of disposable slide mailer, long used for forwarding specimen slides to a clinical laboratory, is made of relatively thin corrugated cardboard. A single elongated rectangular sheet of the cardboard material is divided by transverse score lines into three panels. One end panel is folded against the middle panel and glued together to make a base portion of the slide mailer. One or more elongated openings are cut in this one end panel, which when folded onto the middle panel, define slide holding wells, each dimensioned to closely receive one specimen slide. The third panel, which is the other end panel, is hinged to the middle panel along one or more score lines and can be folded over the base to cover the slide holding well or wells, to retain and protect the specimen slides. The cover is secured to the base of the mailer in its closed, folded condition by means of a small piece of adhesive tape or the like.

This basic type of slide mailer has been in common usage for decades. While such specimen slide mailers are economical and easy to make, they suffer from certain shortcomings with regard to convenience of usage and protection of the specimen material.

Firstly, the slide mailer must be opened i.e., the cover lifted from the base of the mailer, in order to examine the identifying information markings on the specimen slide. This may need to be done more than once at the laboratory, particularly in large clinical laboratories, where each slide mailer is processed through a number of administrative stages before reaching the specimen analysis station, such as a microscope station, where the specimen is subjected to microscopic examination. Each time the slide mailer is opened there is a risk of the slide falling out of its holding well. Such incidents in fact happen with some regularity in most laboratories as a result of simple human fallibility, notwithstanding the high level of care with which the specimens are normally handled. If the thin glass slide falls and breaks, a new specimen must be obtained from the originating physician, who in turn must call in the patient for a repeat visit. Patients in apparent good health frequently give a low priority to such a request from their physician, and a new specimen may not be obtained for weeks or months. Occasionally, this delay allows an incipient illness to progress from an easily curable stage to a less treatable advanced condition, with possible loss of life.

A second shortcoming of current cardboard slide mailers is that the biological specimen is exposed to contact with the inner surface of the mailer's cover during transport, as there is nothing to restrain the slide in its holding well away from the overlying cover. Such contact is undesirable because of the resulting possible loss of specimen material transferred from the slide surface onto the cover. In early stages of a disease, a positive diagnosis may depend on detection of an abnormality present in a small part of the specimen material. If this particular portion of the specimen happens to be lost due to this deficiency in the mailer package, a false negative diagnosis may result, eventually leading to unnecessary late stage treatment of disease and occasional loss of life.

A continuing need exists for low cost disposable slide mailers, particularly corrugated cardboard and paper product slide mailers, which obviate the need for opening the slide mailer in order to view identifying information marked on specimen slides, and which protect the medical specimen against contact with the cover of the slide mailer, all in order to better protect and preserve the specimen material.

SUMMARY OF THE INVENTION

The present invention addresses these shortcomings and concerns in the prior art by providing a mailer for medical specimen slides made of a sheet of relatively stiff material which is cut, scored and folded to make a base and a cover joined along a hinge line for movement between an open and a closed position. The base includes a double thickness of the sheet material, an inner thickness in the base being cut to define one or more holding wells each sized to closely receive a medical specimen slide.

The cover of the slide mailer also has a double thickness of the sheet material, including an inner thickness and an outer thickness of the sheet material, the inner thickness in the cover being cut to define a clearance recess overlying a portion of the well normally occupied by a specimen bearing portion of the specimen slide to be placed in the holding well, and including a restraint for retaining each specimen slide in its corresponding holding well and substantially out of the clearance recess in the cover when the cover is closed against the base of the mailer.

In the presently preferred form of the invention, the cover is cut to define one or more window openings positioned for exposing to view an end portion of each holding well in the closed position of the cover. The end portion normalize contains the indicia bearing portion of the specimen slide placed in the holding well, which is then exposed to view through the window opening without lifting the cover from its closed condition. In this form of the invention, the window is cut through the double thickness of the cover.

The restraint provided for each holding well may consist of an integral portion of the inner thickness of the cover cut so as to overlie the corresponding holding well in the base. The integral portion of the inner thickness may extend across the holding well, and in a presently preferred form of the invention, the restraint is a cross-bar defined between two cut out portions in the inner thickness, the cross-bar being transverse to a longitudinal dimension of each holding well. The two cut out portions may include the clearance recess and the window opening in the cover, both positioned in register with the corresponding holding well.

The present invention also contemplates a mailer for medical specimen slides in which no window opening is provided but having a cover with a recess overlying each holding well in the base and a restraint for retaining the specimen slide in each holding well away from contact with he cover.

These and other advantages, features and improvements according to the present invention will be better understood by reference to the following description of the preferred embodiments taken together with the accompanying drawings.

BRIEF DESCRIPTION OF THE DRAWINGS

FIG. 1 is a perspective view showing the slide mailer according to this invention;

FIG. 1a shows the slide mailer of FIG. 1 unfolded to display the four panels of the mailer;

FIG. 2 shows the slide mailer of FIG. 1 in its closed condition and secured for mailing with adhesive tape;

FIG. 3 is a sectional view of the slide mailer taken along line 3—3 in FIG. 1;

FIG. 4 is a sectional view of the closed mailer taken along line 4—4 in FIG. 2;

FIG. 5 shows an alternate form of the slide mailer without window openings.

DETAILED DESCRIPTION OF THE PREFERRED EMBODIMENTS

With reference to the drawings, FIG. 1 illustrates a medical specimen slide mailer, generally designated by the numeral 10, which has a base portion 12 and a cover portion 14 hinged to each other along a score line 16 for movement between an open condition illustrated in FIG. 1 and a closed condition shown in FIG. 2.

The mailer is made of a single sheet 18 of relatively thin corrugated cardboard or equivalent paper product. The single sheet 18 is shown unfolded in FIG. 1A where it is seen to include four rectangular panels, namely, two opposite end panels 20a and 20d each joined along fold lines 22a, 22b, respectively, to a corresponding center panel 20b and 20c. The center panels 20b and 20c are hingedly joined to each other along the hinge line 16.

The end panel 20a has two well openings 24a, 24b generally shaped as elongated rectangles, parallel to each other and aligned with the longitudinal dimension of the sheet 18, transversely to the hinge line 16. One end of each well opening 24a, 24b, has an arcuate extension 26, the purpose of which will be explained below.

The opposite end panel 20d has four rectangular openings which include two window cut-outs 28a, 28b and two relief cutouts 30a and 30b. Each window cut-out defines with its corresponding relief cut-out a cross-bar 32a, 32b, respectively. Center panel 20c has two rectangular window cutouts 34a, 34b.

It will be appreciated that all of the openings and score lines, fold lines or hinge lines of the sheet 18 as shown in FIG. 1A are formed in a single die cutting operation in a manner which is well-known in the packaging industry. Assembly of the slide mailer 10 involves folding the end panel 20a against the panel 20b as suggested by arrow A in FIG. 1A and then gluing or otherwise permanently securing these two panels in folded-together condition, to make the base 12 as shown in FIG. 1. When so folded, panel 20b provides a bottom for the two well openings 24a, 24b to define two elongated, shallow slide holding wells 36a, 36b. The depth of the holding wells is determined by the thickness of the sheet 18, which is selected to be approximately equal or slightly greater than the thickness of the specimen slide S to be contained in each of the holding wells. The extension 26 in each holding well allows fingertip access to one edge of the specimen slide S in the well, to facilitate lifting the slide out of the well.

Assembly of the slide mailer is completed by folding the opposite end panel 20d against panel 20c and permanently joining the two panels in folded-together relationship, as by gluing, to make the cover 14 shown in FIG. 1. The window cut-outs 28a, 28b in the end panel 20d line up and are in register with the window cut-outs 34a, 34b in panel 20c when the cover 14 is assembled, to define two window openings 38a, 38b through both thicknesses 20c, 20d of the cover 14. The panel 20c also provides a bottom for the two relief cut-outs 38, 30b, to define two overhead clearance recesses 40a, 40b in the cover 14. In the assembled condition of FIG. 2 the base 12 and cover 14 each have a double thickness of sheet material. Panels 20a, 20d constitute the outer thicknesses and panels 20b, 20c the inner thicknesses of the base and cover respectively.

The medical specimen slide S is an elongated rectangle of thin glass, and has an end portion N which is frosted to accept writing or other identifying indicia applied with a suitable marker. The end portion N takes up approximately one quarter of the length of the slide. The remainder of the slide surface D is of clear glass and is the specimen bearing portion of the slide.

Although only one slide S is shown in FIG. 1 for simplicity, the slide mailer 10 is normally supplied with a clean slide S in each holding well 36a, 36b. Each slide is normally oriented with its indicia bearing end N towards the fingertip extension 26, to avoid touching of the specimen bearing area during removal of the slide from the mailer at the laboratory.

Once the medical specimens are deposited on the slide surface D, the mailer 10 is closed by folding the cover 14 over the base 12 along the hinge line 16, to a closed condition illustrated in FIGS. 2 and 4. A short length of adhesive tape 42 applied over the adjacent free edges of the base and cover secures the mailer 10 in its closed condition until the tape is broken at the laboratory to permit access to the specimen slides.

In the closed condition, the two window openings 38a, 38b overly the indicia bearing end portions N of the slides S in the corresponding holding wells, 36a, 36b. The indicia bearing portion N of each slide is exposed to view and easy inspection without opening the slide mailer 10.

FIG. 4 is a cross sectional view of the closed mailer 10, taken along the length of one specimen slide S in its holding well 36a. This drawing best illustrates the improved specimen protection offered by the mailer 10. The clearance recess 48 is seen to overly the specimen bearing portion D of the slide S, providing overhead clearance for the specimen. Additionally, the slide S is retained in its holding well 40a by the restraining cross-bar 32a which bears down on the slide when the cover 14 is closed against the base 12, as the thickness of the cross-bar 32a is the thickness of the sheet 18 and is integral with this sheet. The restraining cross-bar 32a contacts the slide S approximately along the dividing line L between the specimen bearing portion D and the indicia bearing portion N of the slide. At this location, the cross-bar neither obscures markings on the area N nor comes into contact with specimen material which is normally applied away from the area N of the slide.

The relief cut-outs 40a, 40b have a length and width similar to the equivalent dimensions of the specimen bearing area D of the slide, such that the entire specimen bearing area of the slide is afforded overhead clearance. The width and length of the window openings 38a, 38b of the mailer 10 are substantially co-extensive with the indicia bearing surface N of the specimen slide, so as to permit visual inspection of the entire area N with the mailer closed. In effect, each relief cut-out 30a, 30b is separated from a corresponding window cut-out 28a, 28b by the corresponding restraint bar 32a, 32b. Each relief cut-out with its corresponding window cut-out defines an elongated rectangle which is divided by the respective cross-bar and which is of length and width similar to the same dimensions of the corresponding holding well 36a, 36b and in register therewith in the closed condition of the mailer 10.

It should be appreciated that the present invention is not limited to the particular mailer configuration illustrated in FIGS. 1–4. The mailer 10 can be constructed to hold different numbers of specimen slides, from a single slide to a dozen or more, by simply providing the desired number of slide holding wells in a side-by-side or other arrangement, with a relief cut-out and restraining bar for each slide holding well. Preferably a window opening is provided in the cover for each holding well in the base. The mailer 10 is not limited to a side-by-side arrangement of the holding wells. More than one row of slide holding wells can be provided, with corresponding multiple rows of relief cut-outs, restraining bars and window openings in the cover. The restraining bars may be replaced with other forms of restraint elements of different shapes, as for example, one or more portions integral with the end panel 20d and extending into overlying relationship with the corresponding slide holding well so as to bear down on a relatively small surface portion of a slide S contained in the holding well, so as to keep the slide in the holding well and substantially out of the overhead clearance recess space. While it is convenient to make the slide restraint integral with the sheet 18, a separate restraining element may be provided for this purpose as well.

The most common and well accepted material in use for the manufacture of this general class of slide mailers is a thin but relatively stiff corrugated cardboard. Such materials are widely used for conventional disposable slide mailers lacking the improvements of the present invention. However, this invention is not limited to corrugated cardboard materials and other paper and non-paper products will be found similarly suitable for the practice of this invention.

An alternate form of the slide mailer 10 is illustrated in FIG. 5, which is similar to that described in connection with FIGS. 1–4, except in that window cut-outs 28a, 28b, 34a, 34b have been omitted so that no window openings are provided for viewing identifying indicia on the surface portion N of specimen slides S contained in the holding wells 36a, 36b. However, relief cut-outs 38a, 30b are provided as described above, to define an overhead clearance space over the specimen bearing surface portion D of the specimen slide in each holding well. In this form of the invention, the slide restraint is provided by the uncut areas 44a, 44b of the end panel 20d which overlie the indicia bearing portions N of the specimen slides in their respective holding wells.

These and other changes, modifications and substitutions to the preferred embodiments of the invention described above will become apparent to those possessed of ordinary skill in the art without thereby departing from the spirit and scope of the present invention, which is defined by the following claims.

What is claimed is:

1. A mailer for medical specimen slides comprising: a sheet of relatively stiff material cut, scored and folded to make a base and a cover joined along a hinge line for movement between an open and a closed position, said base including a double thickness of said sheet material, one thickness in said base being cut to define a slide holding well sized to closely receive a medical specimen slide, said cover also having a double thickness including an inner thickness and an outer thickness of said sheet material, one thickness in said cover being cut to define a clearance recess overlying said holding well in said closed position, said recess being sized and shaped to avoid contact of said cover with a specimen bearing portion of said specimen slide, and means for restraining said slide in said holding well and out of said recess in said closed position.

2. The mailer of claim 1 wherein said cover is cut to define a window opening positioned for exposing to view an end portion of said holding well in said closed position of the mailer.

3. The mailer of claim 2 wherein said window opening is cut through said double thickness of said cover.

4. The mailer of claim 1 wherein said means for restraining comprise a portion of said inner thickness overlying said holding well.

5. The mailer of claim 4 wherein said portion of said inner thickness extends across said holding well.

6. The mailer of claim 5 wherein said portion of said inner thickness is a cross-bar transverse to a longitudinal dimension of said holding well.

7. The mailer of claim 6 wherein said recess is of elongated shape and in register with said holding well.

8. The mailer of claim 7 wherein said cross-bar separates a window cut-out from a relief cut-out in said inner thickness.

9. A mailer for medical specimen slides comprising:

a sheet of relatively stiff material cut, scored and folded to make a base and a cover joined along a hinge line for movement between an open and a closed position, said base and said cover each having a double thickness of said sheet material including an inner thickness and an outer thickness, the inner thickness in said base being cut to define one or more holding wells each sized to closely receive a medical specimen slide, the inner thickness in said cover having one or more relief cut-outs defining a clearance recess overlying each said holding wells in said closed position, said recess being sized and shaped to avoid contact of said cover with a specimen bearing portion of a said specimen slide, and restraining means integral with said inner thickness of said cover portion overlying each said one or more holding wells for restraining said slide in each said holding well and out of said recess in said closed position.

10. The mailer of claim 9 further comprising one or more window openings in said cover positioned for exposing to view an end portion of each said holding well in said closed position of the mailer, and wherein said each said restraining means comprises a cross-bar transverse to a longitudinal dimension of said holding well, each said cross bar separating said one said relief cut-out from one said window opening.

11. The mailer of claim 10 wherein said each said relief cut-out is of rectangular shape and in register with a corresponding one said holding well, and said cross-bar divides said relief recess from said window opening.

12. The mailer of claim 9 wherein said sheet is divided into four panels, two of said four panels being permanently joined to form said inner and outer thicknesses of said base, and another two of said four panels being permanently joined to form said inner and outer thicknesses of said cover.

13. The mailer of claim 9 wherein said sheet is of relatively thin corrugated cardboard.

* * * * *